(12) United States Patent
Plamann et al.

(10) Patent No.: US 8,398,237 B2
(45) Date of Patent: Mar. 19, 2013

(54) DEVICE AND METHOD FOR OPTICALLY MEASURING THE TRANSMISSION AND DIFFUSION OF OCULAR MEDIA

(75) Inventors: Kartsen Plamann, Palaiseau (FR); Florent Aptel, Laxou (FR); Caroline Crotti, Paris (FR); Florent Deloison, Paris (FR); Donald Peyrot, Limours (FR)

(73) Assignees: Ecole Polytechnique, Palaiseau (FR); Centre National de la Recherche Scientifique, Paris (FR); Ecole Nationale Superieure de Techniques Avancees, Paris (FR)

( * ) Notice: Subject to any disclaimer, the term of this patent is extended or adjusted under 35 U.S.C. 154(b) by 246 days.

(21) Appl. No.: 13/062,597
(22) PCT Filed: Sep. 8, 2009
(86) PCT No.: PCT/FR2009/051693
§ 371 (c)(1),
(2), (4) Date: Mar. 7, 2011
(87) PCT Pub. No.: WO2010/026358
PCT Pub. Date: Mar. 11, 2010

(65) Prior Publication Data
US 2011/0157551 A1 Jun. 30, 2011

(30) Foreign Application Priority Data
Sep. 8, 2008 (FR) .................................. 08 56011

(51) Int. Cl.
*A61B 3/14* (2006.01)
*A61B 3/10* (2006.01)
*A61B 3/00* (2006.01)
(52) U.S. Cl. ......... 351/206; 351/213; 351/221; 351/246
(58) Field of Classification Search .................. 351/206, 351/213, 221, 246
See application file for complete search history.

(56) References Cited

U.S. PATENT DOCUMENTS
2005/0213037 A1  9/2005  Abdullayev et al.

FOREIGN PATENT DOCUMENTS
WO       01/47426 A1      7/2001
WO    2004/089200 A1    10/2004

OTHER PUBLICATIONS
International Search Report, dated Dec. 8, 2009, from corresponding PCT application.

*Primary Examiner* — Jack Dinh
(74) *Attorney, Agent, or Firm* — Young & Thompson (57) ABSTRACT

An optical device for measuring the transmission and diffusion of a tissue of the front segment of an eye, includes: a light source; an optical collimation system for directing the collimated light beam towards a tissue of the front segment of an eye to be characterized; an optical mire placed on the optical path between the optical collimation system and the tissue; an optical imaging system capable of receiving a light beam transmitted by the mire and the tissue and capable of forming an image of the mire on an image detector; and an image processing system capable of calculating a modulation transfer function for the tissue from an image of the mire through the ocular medium. The optical mire includes a set of alternately light and dark angular sectors radially distributed from a central point. Different image processing methods for extracting a function representing the transmission and diffusion characteristics of the tissue are described.

19 Claims, 6 Drawing Sheets

DEVICE AND METHOD FOR OPTICALLY MEASURING THE TRANSMISSION AND DIFFUSION OF OCULAR MEDIA

The present invention relates to a device and a method for optically measuring the transmission and diffusion of ocular media of the front segment of the eye. These ocular media can be solid media such as the cornea or a cornea graft, the sclera, the crystalline lens, or liquid media such as the aqueous humor or the vitreous body.

The surgery of the front segment of the eye relates in particular to the cornea grafts. Several tens of thousands of cornea grafting operations are performed each year in the developed countries. In a cornea graft operation, the pathologic cornea of the patient is removed and replaced by a cornea graft coming from a donor. Before the transplantation, an important number of corneas are harvested from the donors. For their qualification as potential grafts, these harvested corneas are subjected to a number of biological, chemical and physical tests. The grafts are then preserved in a preservative liquid at eye banks, up to their implantation.

The cornea can be likened to a slightly diverging lens that participates to the formation of the image on the retina. Generally, the optical quality of the donor grafts, i.e. the transparency thereof, is macroscopically controlled by an ophthalmologist surgeon of the eye bank. However, this assessment is subjective and may vary from one intervener to one another. Moreover, the different eye banks have sometimes to exchange grafts with each other, but they do not have normalized measurement procedures.

There exists a need for quantitatively and automatically measuring the optical quality of the cornea grafts. In order to optimize the classification of grafts, normalize the procedure and increase the reproducibility thereof, it would indeed be very useful if the optical quality of these tissues could be automatically and objectively determined and if this method was normalized with respect to the different subjective systems of classification.

A device for measuring the transmission of cornea grafts is described in L. Ventura et al., *Portable Light Transmission Measuring System for Preserved Corneas*, BioMedical Engineering OnLine 4:70 (2005). This system measures the intensity of an optical beam transmitted by a sample, integrating this intensity in the spatial domain over the whole lighted surface and in the spectral domain over a spectral range of 400 to 700 nm. This measurement is normalized using a similar measurement performed without sample, to obtain the transmittance of the cornea. This simple system thus makes it possible to measure rapidly the optical transmission of a cornea graft and to classify the corneas into different categories based on this transmittance. However, this measuring system measures exclusively the transmittance and does not provide information about a potential diffusion of the measured cornea.

Yet, the cornea is a fragile organic medium that is liable to deteriorate in vivo or after harvesting, in a preservative liquid. When the cornea or the cornea graft absorbs too much water, the cornea or the graft may become oedematous. The cornea then presents not only surface diffusion but also volume diffusion. It is important that the grafts are sorted out so as not to transplant grafts presenting a risk of oedema for the patient. Therefore, it seems that it is necessary to measure not only the transmittance but also the diffusion of each potential cornea graft.

Up to now and to the best of our knowledge, there is no commercially available device providing a rapid and normalized measurement of the transmission and diffusion of cornea grafts. It would be useful if these cornea grafts could be measured at several moments: immediately after harvesting, so as to keep only the grafts having sufficient optical qualities, and before implantation, so as to eliminate the grafts whose optical transmission and/or diffusion properties have been deteriorated. This measurement should be able to be carried out by a laboratory technician, without needing assessment of an ophthalmologist surgeon.

The document WO/2004/089200 describes a device for measuring in vivo the optical quality of the front segment of the eye of a patient. This device measures an optical beam transmitted and/or reflected by the successive interfaces of the cornea and the crystalline lens. More precisely, this device forms the image of a series of ten parallel dashed lines after refraction/reflection of the incident beam. The dashes are of same length on a same line and of different length from one line to another. The length of the shortest dashes corresponds to the maximum resolution of the front segment of the eye, while the length of the longest dashes is about ten times the length of the shortest ones. The image of the lines is analysed to determine a modulation transfer function for the front segment of the eye as a function of ten spatial frequencies of the series of lines. However, this device operates in a reflective way over all the front segment of the eye but it does not permit the volume diffusion of a cornea to be measured. Thereafter, the provided results seem difficult to correlate with an assessment of the optical quality of the eye: the MTF measurement of deteriorated eye (FIG. 10) seems higher at the high spatial frequencies than the MTF of a normal patient (FIG. 8). Finally, the number of spatial frequencies is limited by the number of lines.

A publication of P. Gain (Acta Ophthalmologica Scandinavica 2007, Vol. 45, Issue 240) discloses an apparatus for analysing images of cornea grafts for the measurement of transparency (T), fold number (to derive therefrom the folding degree) (F) and the degree of gerontoxon, i.e. the diameter of the light central section of the cornea (G). For that purpose, the digital image of a retro-illuminated chart comprising parallel lines viewed through the cornea is analysed using dedicated software. T (%) is the ratio between the local contrast of the mire and F (%) is the ratio of the mean profile of the lines, each being measured with and without a cornea. For each criterion T, F and G, an image can be classified by experts into three categories of quality. However, this abstract does not describe how to obtain a measurement that is indicative of the cornea diffusion. The alignment of the chart to the optical axis of the apparatus is not either described. Moreover, according to this method, the cornea measurement is carried out in a "flat configuration", which is liable to induce an additional folding of the cornea, which then constitutes a measurement artefact.

The invention mainly (but not exclusively) addresses the problem of the optical transmission and diffusion characterization of cornea grafts. A simple device for transmission and diffusion quantification may also be useful in other applications than the cornea grafts, in particular in the measurement of other tissues of the front segment of the eye (sclera, crystalline lens, eyeball).

The present invention has for object to remedy these drawbacks and, more particularly, it relates to a device and a method for optically measuring the transmission and diffusion of tissues of the front segment of the eye. The device permits an objective assessment of ocular media, even diffusive ones.

The invention relates to an optical device for measuring the transmission and diffusion of a tissue of the front segment of an eye, said device comprising at least one light source capable of emitting a light beam, an optical collimation system capable of directing the collimated light beam towards a tissue of the front segment of an eye to be measured, an optical mire placed on the optical path between the optical collimation system and the front segment tissue, an optical imaging system capable of receiving a light beam transmitted by the mire and by the front segment tissue and capable of forming an image of the mire on an image detector, and an image processing system capable of calculating a modulation transfer function for the tissue from an image of the mire through the tissue. According to the invention, the optical mire comprises a set of alternately light and dark angular sectors radially distributed from a central point (O).

According to a particular embodiment of the invention, the optical mire comprises a set of 2.N angular sectors having the same angular opening $\alpha = 180°/N$.

According to a particular embodiment, the device of the invention comprises a spatial filter between the source and the optical collimation system. The measuring device of the invention may also comprise a light source capable of emitting a light beam comprising a plurality of wavelengths and a wavelength filtering means for measuring the transmission and diffusion of a tissue of the front segment of an eye as a function of the wavelength.

According to a particular embodiment, the device of the invention comprises a sample carrier capable of receiving a tissue of the front segment of an eye, from the following ones: cornea, cornea graft, crystalline lens, sclera, aqueous humor, vitreous body.

The device advantageously comprises a comparator capable of comparing the modulation transfer function for a tissue of the front segment of an eye to a set of reference curves.

The invention also relates to a method for measuring the transmission and diffusion of a tissue of the front segment of an eye, comprising the following steps:
  emitting a light beam from a light source,
  collimating the light beam using an optical system,
  transmitting the collimated beam through an optical mire,
  transmitting the optical beam spatially modulated by the mire through the tissue (7) of the front segment of an eye to be measured,
  forming and acquiring an image of the mire through the tissue of the front segment of an eye; and:
  processing the image of a mire comprising a set of alternately light and dark angular sectors radially distributed from a central point (O) by a Fourier transform operation, to derive therefrom the modulus of a modulation transfer function for a tissue of the front segment of an eye as a function of the spatial modulation frequencies of the mire.

According to a first embodiment, the measuring method comprises the following steps of image processing:
  two-dimensionally Fourier transforming the image of the mire to derive therefrom a spectrum measurement of the image of the tissue of the front segment of an eye as a function of the continuous or discrete set of spatial modulation frequencies of the mire,
  normalizing this spectrum with respect to the spectrum of an image of the mire obtained without the tissue to obtain a curve of the modulus of the modulation transfer function (MTF) of the tissue of the front segment of an eye.

According to a second embodiment, the measuring method comprises the following steps of image processing:
  analysing the image of the mire according to a series of rings of centre $0'$ and radius r ($0 < r < R_{MAX}$),
  determining the modulation rate of each ring by adjusting a sinusoidal function, and
  calculating the modulus of the modulation transfer function as a function of the spatial frequencies corresponding to each of said rings,
  normalizing with respect to a MTF curve without sample.

According to a third embodiment, the measuring method comprises the following steps of image processing:
  analysing the image of the mire according to a series of rings of centre $0'$ and radius r ($0 < r < R_{MAX}$),
  projecting the intensity of each ring in a matrix of polar coordinates (r, $\theta$),
  converting the axe r into a spatial frequency $\nu$, to obtain a matrix in coordinates ($\nu$, $\theta$),
  applying a one-dimensional Fourier transform for each row,
  determining the column vector corresponding to the fundamental harmonic $\omega_0$ of modulation of the mire,
  calculating the modulus of the modulation transfer function (MTF) based on values of the column vector at the frequency $\omega_0$, as a function of the spatial modulation frequencies $\theta$ corresponding to each of said rings,
  normalizing the modulus of the modulation transfer function with respect to a measurement without sample.

The present invention also relates to the characteristics that will become evident in the following description and that will have to be considered either alone or in any technically possible combination.

The present description is given only by way of non-limitative example and will permit to better understand how the invention can be implemented with reference to the appended drawings, in which.

Figure 1:
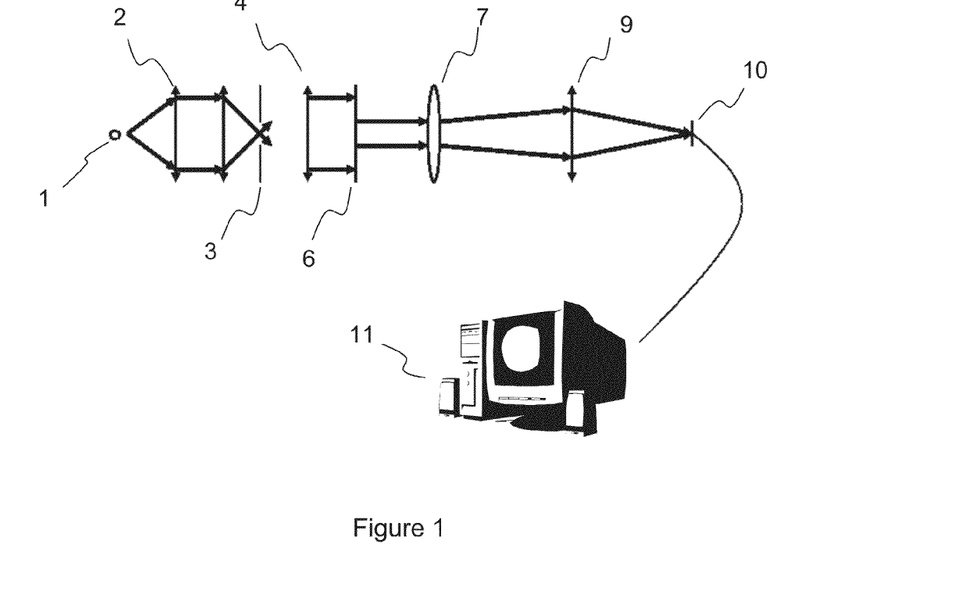
FIG. 1 schematically shows a measuring device according to the invention.

An embodiment of the measuring device of the invention is shown in FIG. 1. According to this embodiment, the device comprises a lighting section for lighting the sample 7 through a mire 6 and an imaging section for imaging the mire through the sample. The lighting system comprises a light source 1, provided for example with a diffuser, an optical system 2, a spatial filtering system 3 and a collimation lens 4. The light source that illuminates the sample can cover all or part of the visible or near infrared spectrum or be monochromatic. This lighting system makes it possible to uniformly illuminate a mire 6. A uniform illumination can be implemented for example by a Köhler geometry. If the light source does not emit light uniformly, it is possible to use an optical diffuser. A possible embodiment can make it possible to choose the wavelength by introducing filters or selecting one from several sources (blue, green, red LEDs . . . ) to determine the transparency as a function of the spectral range.

Figure 2:
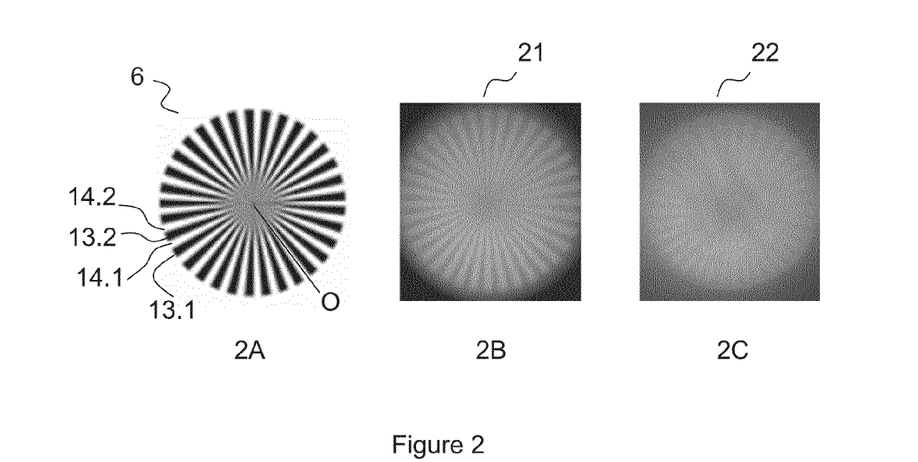
FIG. 2A schematically shows a radial-modulation optical mire used in a device of the invention.
FIG. 2B illustrates a first image of the mire obtained by means of the device of the invention in the absence of a sample to be measured.
FIG. 2C illustrates a second image of the mire obtained by means of the device of the invention in the presence of a sample.

The optical mire 6 is preferably radially modulated by a set of angular sectors, the transmission coefficient of which is alternately high and low. Therefore, such a mire comprises a continuous set of spatial modulation frequencies, these spatial frequencies varying monotonically as a function of the distance to the mire centre. The spatial modulation frequency is higher at the mire centre (O). The mire 6 is advantageously centrosymmetric. It is preferably a mire known as "Siemens test chart". The regular centrosymmetric nature of the mire facilitates the alignment thereof to the optical axis of the device.

The sample 7 to be measured is placed just behind the mire 6 or in a conjugated plane. More particularly, the device will be able to be used for determining the transparency of the different media of the front segment of the eye, in particular the cornea. For that purpose, the sample 7 can be placed in a transparent sample carrier filled with serum. The cornea to be measured can be mounted on a device like an "artificial chamber" so as to minimize the appearance of folds on the cornea, which would not be related to the intrinsic properties of the cornea.

The imaging part can be implemented according to one of the numerous standard schemes available in the literature. In the embodiment shown in FIG. 1, an optical system 9 makes it possible to obtain an image 22 of the mire on a camera 10. For the analysis of the cornea, which is naturally equivalent to a slightly diverging lens, the imaging device preferably comprises a correcting lens in order to compensate for the "lens" effect of the cornea.

For each sample 7, the device preferably acquires two images: an image 21 of the mire without sample (FIG. 2B) so as to have a reference measurement of the set of components of the device (optical systems, light source), and an image 22 with the sample in place (FIG. 2C), inserted in the optical bank by means of an adapted sample carrier. The images 21, 22 acquired by the camera 10 are transmitted to an image processing system 11.

These images 21, 22 can be submitted to a pre-processing so as to reduce the noise, increase the contrast, select and centre the area of interest containing the mire in the image. In particular, the centrosymmetric structure of the mire 6 facilitates the recentring of the images, which can be performed automatically. The recentring consists in recentring the image of the mire with respect to the pixel-domain image, both in the case of the image 22 with the sample and in the case of the image 21 without sample. The algorithms used in the following are sensitive to the good positioning of the mire centre at the position "0" at the centre of the image.

The images are then digitally processed according to either one of the different following image processing methods. The three methods of processing the detected image comprise a step of (one-dimensional or two-dimensional) Fourier transforming and analysing in a Fourier space. These processing methods described in more detail hereinafter make it possible to extract from the images 21, 22 a measurement of the modulus of the optical transfer function (MTF) that is representative of both the transmission and the diffusion of the ocular medium measured. The MTF measurement of a sample is normalized with respect to the MTF of the measuring device in the absence of sample. This normalization makes it possible to eliminate the potential defects of the optical system and thus to obtain "objective" information. The standard deviation of the MTF is possibly measured.

The different image processing methods used are schematically illustrated in FIGS. 3 to 12.

The first image processing method consists firstly in applying to the image 22 a Fourier transform operation (two-dimensional FFT), then in normalizing the result by the Fourier transform of the image 21 without sample. More precisely, the two-dimensional figure obtained by FFT is projected onto an axis of spatial modulation frequency, which makes it possible to obtain a curve of the modulation transfer function (MTF) versus spatial modulation frequencies. This MTF curve normalized to the response of the apparatus is representative of the transmission and diffusion properties of the tissue studied. This is the evolution (shape and level) of this curve that will permit to "qualify" the tissue in terms of transparency and diffusion. In a simplified manner, MTF ($v=0$) is representative of the transmission coefficient of the sample, while the attenuation of MTF($v$) increases with the diffusion of the sample as a function of the spatial modulation frequencies. The cross-over frequency indicates the maximal resolution of the sample measured, which is limited in particular by the diffusion.

Figure 3:
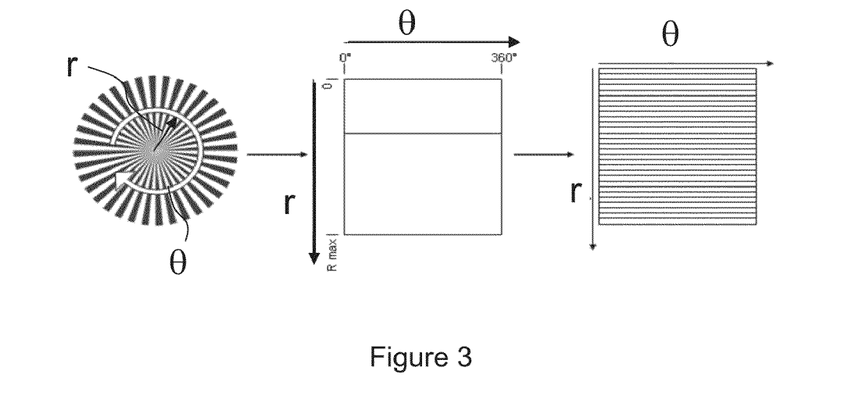
FIG. 3 illustrates a transformation of the detected image into polar coordinates ($\theta$, r)
Figure 4:
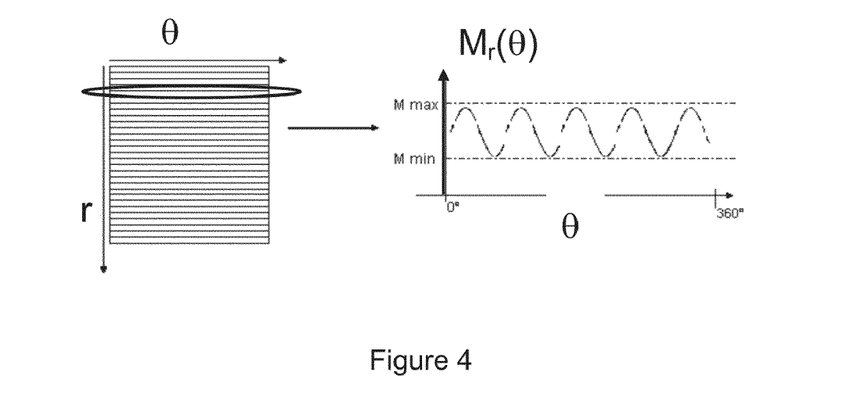
FIG. 4 schematically illustrates a second embodiment of a measurement of the modulation rate for a given radius r, by adjustment of a sinusoidal curve to the detected modulation signal.
Figure 5:
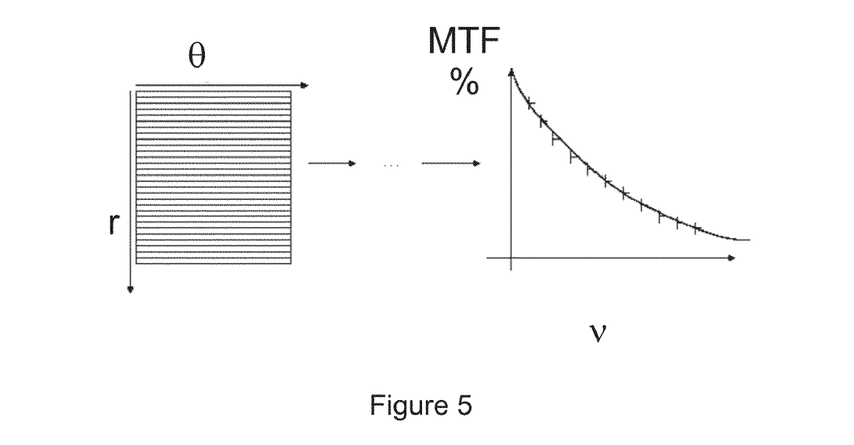
FIG. 5 schematically illustrates a result of measurement of the modulation rate versus the spatial modulation frequency.

The second image processing method is schematically illustrated in FIGS. 3-5. The image 22 is analysed in the real domain by "rings" of mean radius r, and the modulated intensity of which is projected onto a vector as a function of the angle θ. This method is repeated every radii r inside the mire. FIG. 3 illustrates the filling of a matrix of vectors corresponding to the radii of the mire. Thereafter, to each vector (row of the matrix) is applied a step of adjustment of a sinusoidal function (the frequency of the sinusoid is constant because the number of radii is fixed whatever the ring is, the adjustment relates to the value of the sinus curve offset and amplitude). Based on this sinus adjustment, a modulation rate is calculated for each spatial frequency (i.e. each radius analysed, or each vector stored in the matrix) (FIG. 4). The modulation rate value associated with each spatial frequency is then plotted, which permit to obtain the modulus of the modulation transfer function of the tissue studied. This curve is normalized with respect to a MTF curve without sample (FIG. 5). This method also makes it possible to identify a potential annular opacification (gerontoxon) by a spectral "signature" (lowering of a specific frequency band in the MTF). This method also makes it possible to identify a potential localized opacification by the increasing of the standard deviation for a frequency band corresponding to the distance of the opaque area from the mire centre.

Figure 6:
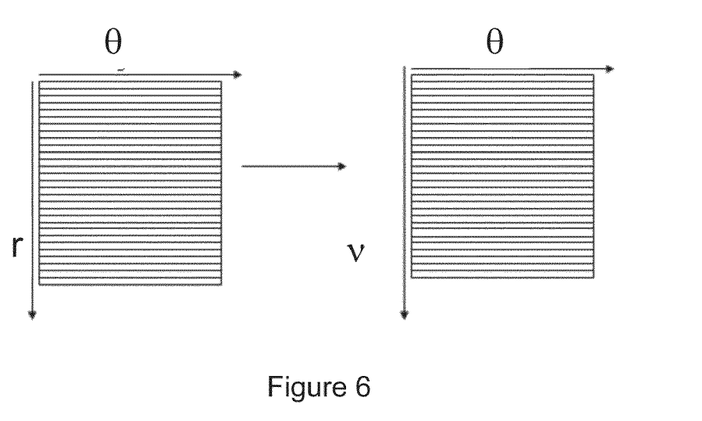
FIG. 6 illustrates the conversion according to one dimension of a matrix of polar coordinates (r, $\theta$) into spatial frequencies ($\nu$, $\theta$)

The third image processing method is schematically illustrated in FIGS. 6-12. The image 22 is also analysed by "rings" of mean radius r, and the modulated intensity of which is projected onto a row vector of a matrix. The projection of the rings of variable radius r makes it possible to build a matrix of values (cf. FIG. 6). The radius r is then converted into a spatial frequency. A spatial frequency $v$ is related to the number N of radii in the mire and to the mean radius r of the ring and to the optical magnifying power of the imaging system G, according to the formula:

$$\nu = 2N/(G \cdot 2 \cdot \pi \cdot r).$$

Figure 7:
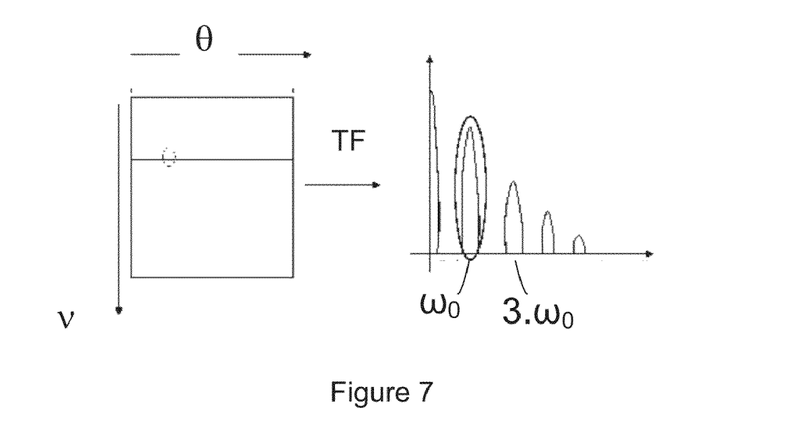
FIG. 7 illustrates the representation of an intermediate step of the third embodiment of the invention.
Figure 8:
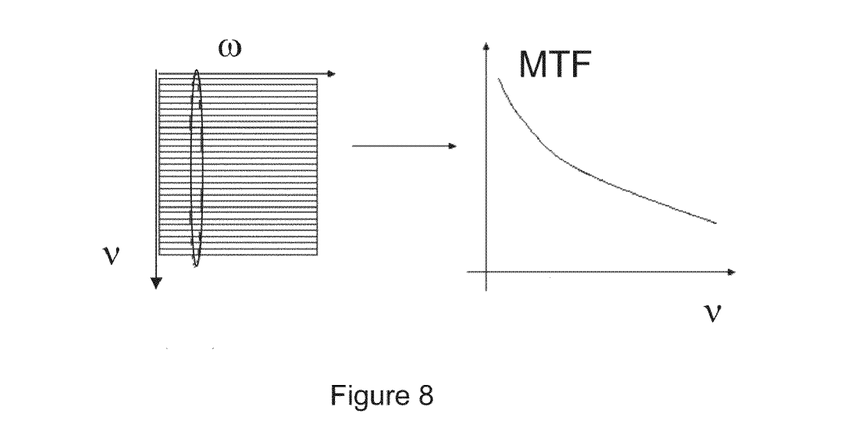
FIG. 8 schematically illustrates a curve of measurement of the modulation transfer function versus the spatial frequency.
Figure 9:
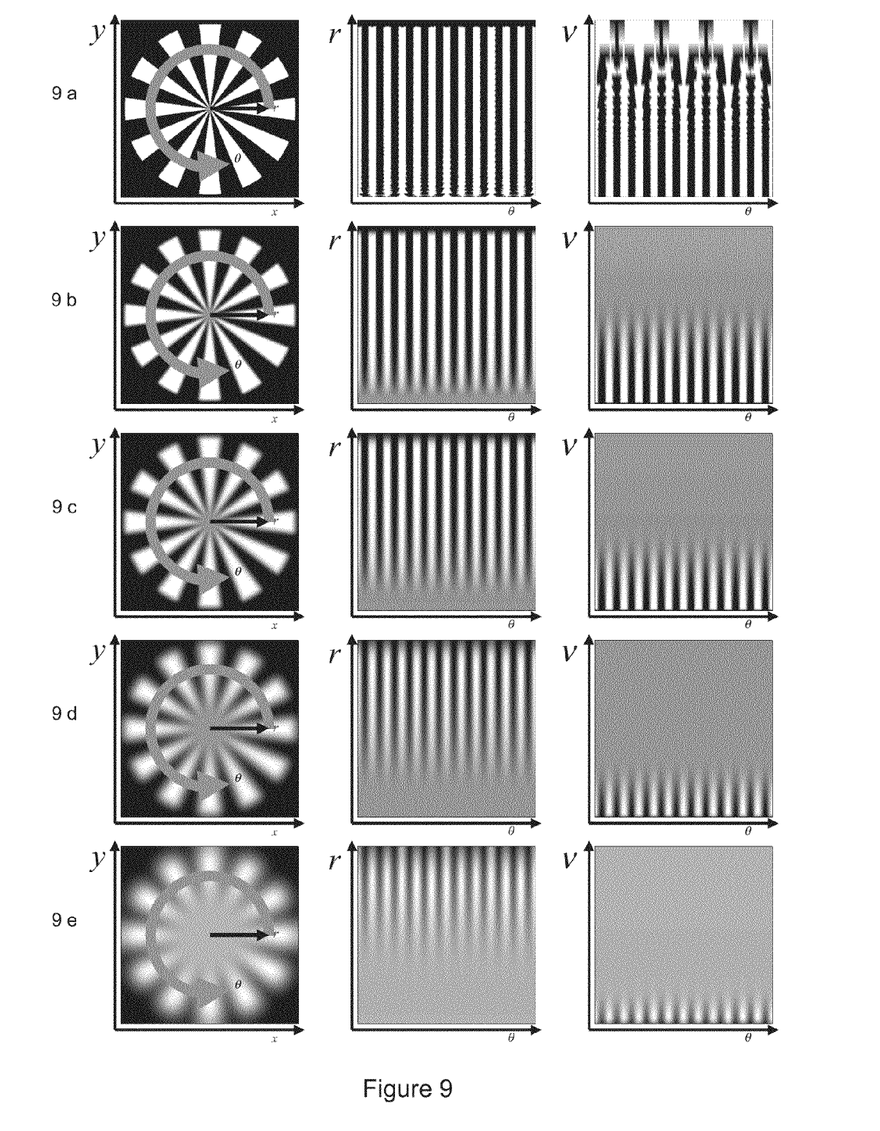
FIG. 9 shows a simulation of measurement of samples of increasing diffusion (a, b, c, d, e) and processed according to the third embodiment.
Figure 10:
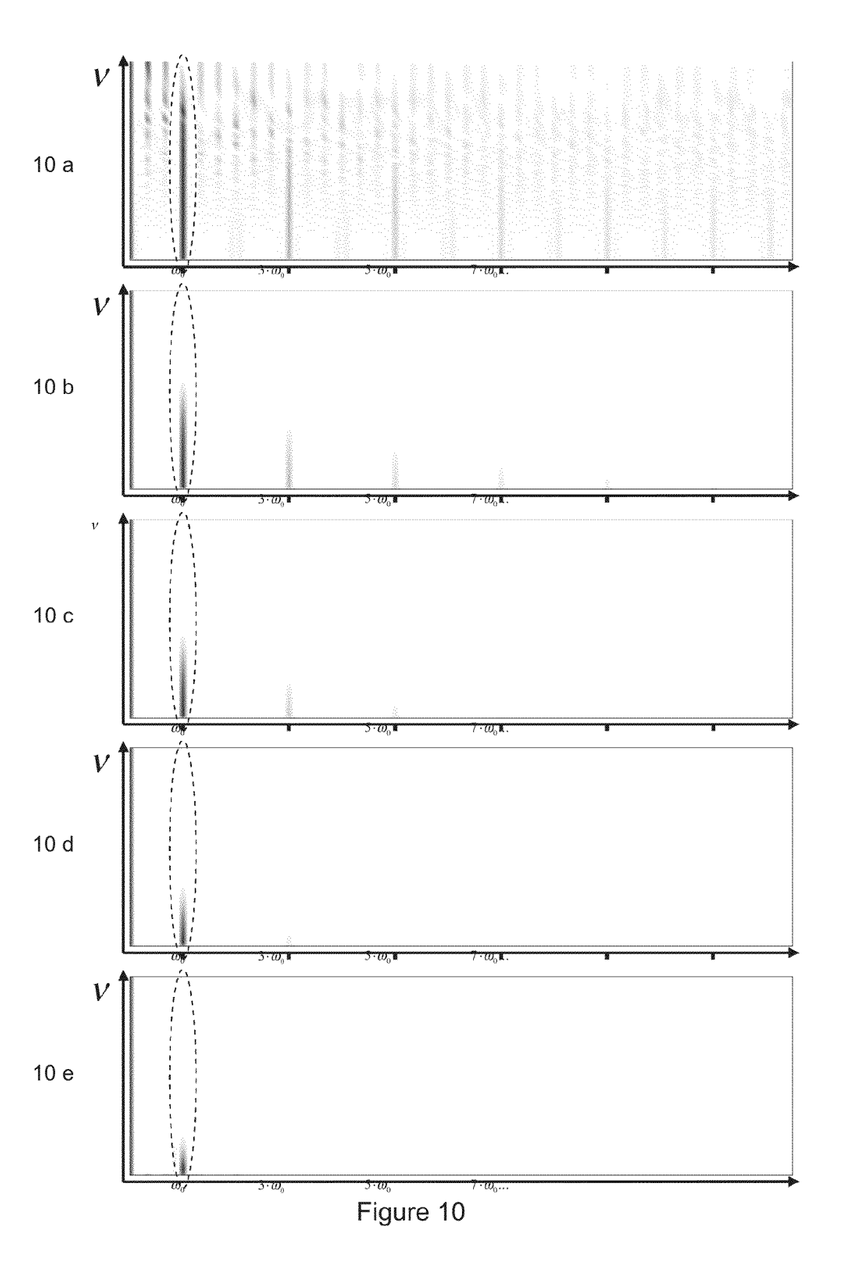
FIG. 10 shows the analysis results of the harmonic modulation for the different samples a) to e) of FIG. 9.
Figure 11:
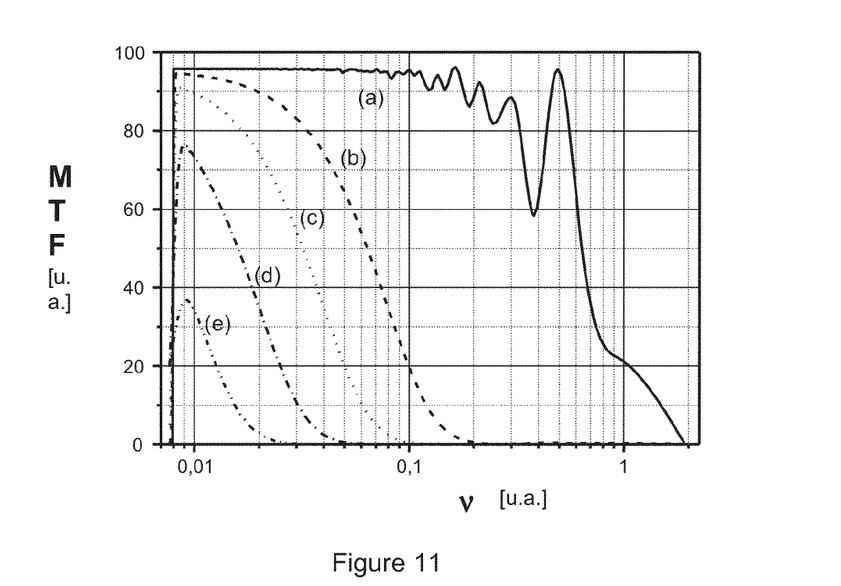
FIG. 11 shows the curves of modulation transfer function of the samples a) to e) versus the spatial modulation frequencies of the mire.
Figure 12:
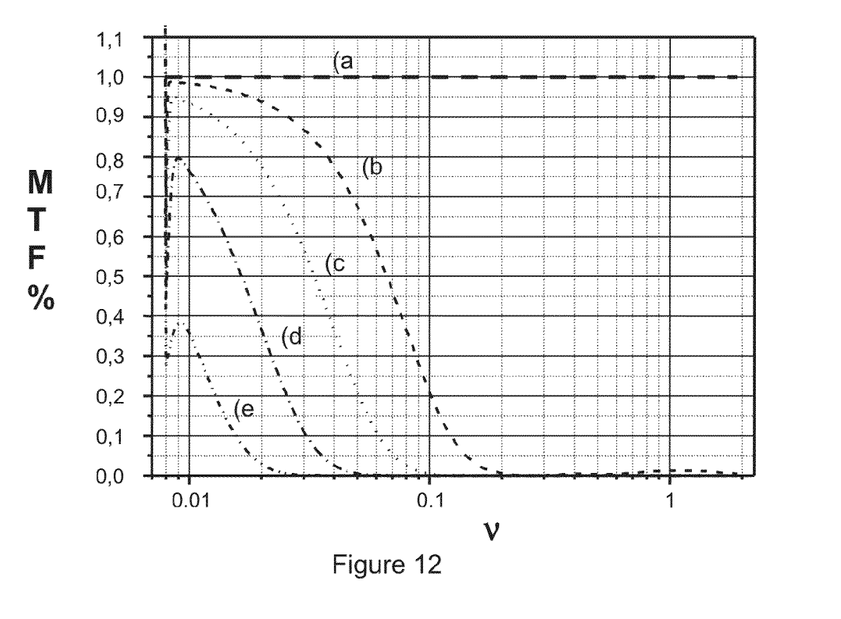
FIG. 12 shows the normalized curves of modulation transfer function of the samples a) to e) versus the spatial modulation frequencies of the mire.

A digital one-dimensional Fourier transform operation is applied to each row vector of the matrix $M(\nu, \theta)$ to obtain a matrix in the spatial modulation frequencies space $M^*(\nu, \omega)$ (cf. FIG. 7). For each column vector corresponding to a modulation frequency $\omega$, the profile can be displayed, which shows the components at various frequencies: frequency zero, fundamental frequency ($\omega_0$) and the harmonics ($3\omega_0$, $5\omega_0$ ...) (cf. FIG. 7). By selecting only the column vector and possibly the neighbour column vectors at the fundamental frequency $\omega_0$ for the considered radius, the values of this vector can be plotted as a function of the spatial frequency, and a modulation transfer function of the tissue studied is thus obtained, which is normalized with respect to a measurement without sample (FIG. 11). The modulation transfer function curves are normalized with respect to the measurement "without sample" (FIG. 12). This procedure can also be performed based on harmonic frequencies, but the signals obtained will then be noisier. This method also makes it possible to identify a potential annular opacification (gerontoxon) by a spectral "signature" (lowering of a specific frequency band in the MTF). This method also makes it possible to identify a potential localized opacification by the increasing of the standard deviation for a frequency band corresponding to the distance of the opaque area from the mire centre.

According to this third method, when the mire is correctly aligned, in principle, only odd harmonics of the fundamental frequency $\omega_0$ are detected: the harmonics $3\omega_0$, $5\omega_0$ ... (cf. FIG. 7). The occurrence of even harmonics ($2\omega_0$, $4\omega_0$ ...) in the spectra indicates an imbalance between light and dark segments of the mire on the camera. This apparent distortion may be due to a dazzle and saturation of the camera sensor or, on the contrary, an underexposure of the sensor. The regular centrosymmetric nature of the mire makes it possible to correct these effects and to obtain a perfect alignment.

These image processing methods can be implemented using software such as MatLab, LabView, or programs or libraries specialized in digital computing and/or image processing.

The signal processing finally comprises a step of classification or normalization with respect to the existing classification systems. The MTF curves obtained for the tissues are compared to abacus curves for samples classified by an ophthalmologist surgeon. This classification may refer to one of the empirical classification systems mentioned in the literature.

A quantitative value characterizing the quality of the normalized MTF curves may also be determined. This can be performed, for example, by comparing the measurements to a bundle of pre-calculated curves or by calculating the integral under the curve and normalizing it with respect to the curve "without sample". In the example shown in FIG. 12, the curves herein simulated provide the values: 0.83 for sample b); 0.68 for sample c); 0.43 for sample d) and 0.15 for sample e), respectively. Accordingly, a single numeric value is determined, which is representative of both the transmission coefficient of the sample and the diffusion of this sample.

These numeric values are mapped to the "subjective" scale obtained by a series of tests involving physicians familiar with the cornea classification.

In the case of ocular tissues, the method is normalized by comparing the results to the existing methods (for the cornea, a bibliographic review may be found in: C. O'Donnell, J S Wolffsohn, *Grading of corneal transparency*, Contact Lens & Anterior Eye 27, 161-170, 2004).

Therefore, the invention makes it possible to classify solids, liquids and diffusing tissues, in particular the tissues of the front segment of the eye, as a function of a curve representative of the transmission and diffusion thereof or as a function of a single parameter characteristic of each curve.

The device further permits to make analysis at different spatial modulation frequencies using, on the one hand, the image of a specific optical mire through the ocular medium to be measured, and on the other hand, an image processing device adapted to the calculation of the optical modulation transfer function of the medium to be measured.

The optical mire used and the processing system make it possible to accurately measure the transfer function of elements of the front segment of the eye as a function of a continuum of spatial modulation frequencies.

The device is advantageously spectroscopic, so that the diffusion can be measured as a function of the wavelength. Indeed, it is known that the diffusion modes depend on the size of the diffusing particles as well as the wavelength (diffusion of Mie, Rayleigh ...). It is therefore interesting that the spectral variations of the diffusion can be studied in order to interpret the origin thereof.

The device of the invention is cheap. This device provides an objective quantification of the transparency and diffusion of the ocular tissues. The quantitative measurement obtained may permit a finer classification than the three categories of cornea transparency usually and subjectively defined by the practitioners.

The algorithms used are robust with respect to the variations of measuring conditions.

The optical device of the invention is simple and may be automatized so that an operator can use it without needing specific knowledge in ophthalmology.

The invention claimed is:

1. An optical device for measuring the transmission and diffusion of a tissue (7) of the front segment of an eye, said device comprising:
    at least one light source (1) capable of emitting a light beam,
    an optical collimation system (2, 4) capable of directing the collimated light beam towards a tissue (7) of the front segment of an eye to be characterized,
    an optical mire (6) placed on the optical path between the optical collimation system (4) and the tissue (7) of the front segment,
    an optical imaging system (9) capable of receiving a light beam transmitted by the mire (6) and by the front segment tissue (7) and capable of forming an image of the mire (6) on an image detector (10), and
    an image processing system (11) capable of calculating a modulation transfer function for the tissue (7) from an image (22) of the mire through the tissue (7),
    characterized in that:
    said optical mire (6) comprises a set of alternately light (13.1, 13.2 ...) and dark (14.1, 14.2 ...) angular sectors (13, 14) radially distributed from a central point (O).

2. A device according to claim 1, characterized in that the optical mire (6) comprises a set of 2.N angular sectors (13.1, 14.1, 13.2, 14.2, ..., 13.N, 14.N) having the same angular opening $\alpha = 180°/N$.

3. A device according to claim 2, characterized in that it comprises a spatial filter between the source and the optical collimation system.

4. A device according to claim 2, characterized in that the light source (1) is capable of emitting a light beam comprising a plurality of wavelengths and in that the device comprises a wavelength filtering means and is capable of measuring the transmission and diffusion of a tissue (7) of the front segment of an eye as a function of the wavelength.

5. A device according to claim 2, characterized in that it comprises a sample carrier capable of receiving a tissue of the front segment of an eye, from the following ones: cornea, cornea graft, crystalline lens, sclera, aqueous humor, vitreous body.

6. A device according to claim 2, characterized in that it comprises a comparator capable of comparing the modulation transfer function for a tissue (7) of the front segment of an eye to a set of reference curves.

7. A device according to claim 1, characterized in that it comprises a spatial filter between the source and the optical collimation system.

8. A device according to claim 7, characterized in that the light source (1) is capable of emitting a light beam comprising a plurality of wavelengths and in that the device comprises a wavelength filtering means and is capable of measuring the transmission and diffusion of a tissue (7) of the front segment of an eye as a function of the wavelength.

9. A device according to claim 7, characterized in that it comprises a sample carrier capable of receiving a tissue of the front segment of an eye, from the following ones: cornea, cornea graft, crystalline lens, sclera, aqueous humor, vitreous body.

10. A device according to claim 7, characterized in that it comprises a comparator capable of comparing the modulation transfer function for a tissue (7) of the front segment of an eye to a set of reference curves.

11. A device according to claim 1, characterized in that the light source (1) is capable of emitting a light beam comprising a plurality of wavelengths and in that the device comprises a wavelength filtering means and is capable of measuring the transmission and diffusion of a tissue (7) of the front segment of an eye as a function of the wavelength.

12. A device according to claim 11, characterized in that it comprises a sample carrier capable of receiving a tissue of the front segment of an eye, from the following ones: cornea, cornea graft, crystalline lens, sclera, aqueous humor, vitreous body.

13. A device according to claim 11, characterized in that it comprises a comparator capable of comparing the modulation transfer function for a tissue (7) of the front segment of an eye to a set of reference curves.

14. A device according to claim 1, characterized in that it comprises a sample carrier capable of receiving a tissue of the front segment of an eye, from the following ones: cornea, cornea graft, crystalline lens, sclera, aqueous humor, vitreous body.

15. A device according to claim 1, characterized in that it comprises a comparator capable of comparing the modulation transfer function for a tissue (7) of the front segment of an eye to a set of reference curves.

16. A method for measuring the transmission and diffusion of a tissue (7) of the front segment of an eye, comprising the following steps:
    emitting a light beam from a light source,
    collimating the light beam using an optical system (2, 4),
    transmitting the collimated beam through an optical mire (6),
    transmitting the optical beam spatially modulated by the mire through the tissue (7) of the front segment of an eye to be measured,
    forming and acquiring an image of the mire (6) through the tissue (7) of the front segment of an eye, and
    characterized in that it comprises a step of:
    processing the image (22) of a mire comprising a set of alternately light (13.1, 13.2 . . . ) and dark (14.1, 14.2 . . . ) angular sectors (13, 14) radially distributed from a central point (O), comprising a Fourier transform operation to derive therefrom the modulus of the modulation transfer function for the tissue (7) of the front segment of an eye as a function of the spatial modulation frequencies of the mire.

17. A measuring method according to claim 16, characterized in that the step of image processing comprises the steps of:
    two-dimensionally Fourier transforming the image (22) of the mire to derive therefrom a spectrum measurement of the image of the tissue (7) of the front segment of an eye as a function of a continuous or discrete set of spatial modulation frequencies of the mire (6),
    normalizing this spectrum with respect to the spectrum of an image (21) of the mire obtained without the tissue (7) to obtain a curve of the modulus of the modulation transfer function (MTF) of the tissue (7) of the front segment of an eye.

18. A measuring method according to claim 16, characterized in that the step of image processing comprises the following steps:
    analysing the image of the mire according to a series of rings of centre 0' and radius r ($0<r<R_{MAX}$),
    determining the modulation rate of each ring by adjusting a sinusoidal function, and
    calculating the modulus of the modulation transfer function as a function of the spatial frequencies corresponding to each of said rings,
    normalizing with respect to a MTF curve without sample.

19. A measuring method according to claim 16, characterized in that the step of image processing comprises the following steps:
    analysing the image of the mire according to a series of rings of centre 0' and radius r ($0<r<R_{MAX}$),
    projecting the intensity of each ring in a matrix of polar coordinates (r, θ),
    converting the axe r into a spatial frequency ν, to obtain a matrix in coordinates (ν,θ),
    applying a one-dimensional Fourier transform for each row,
    determining the column vector corresponding to the fundamental harmonic $\omega_0$ of modulation of the mire,
    calculating the modulus of the modulation transfer function (MTF) based on values of the column vector at the frequency $\omega_0$, as a function of the spatial modulation frequencies ν corresponding to each of said rings,
    normalizing the modulus of the modulation transfer function with respect to a measurement without sample.

* * * * *